(12) United States Patent
Reynaud et al.

(10) Patent No.: US 10,204,786 B2
(45) Date of Patent: Feb. 12, 2019

(54) DEVICE FOR CONNECTING AT LEAST ONE NANO-OBJECT AND METHOD OF MANUFACTURING IT

(71) Applicant: COMMISSARIAT A L'ENERGIE ATOMIQUE ET AUX ENERGIES ALTERNATIVES, Paris (FR)

(72) Inventors: Patrick Reynaud, Murianette (FR); Xavier Baillin, Crolles (FR); Emmanuel Rolland, Jarrie (FR); Aurelie Thuaire, Voiron (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/474,259

(22) Filed: Mar. 30, 2017

(65) Prior Publication Data
US 2017/0294313 A1 Oct. 12, 2017

(30) Foreign Application Priority Data

Apr. 8, 2016 (FR) ...................................... 16 53118

(51) Int. Cl.
*H01L 21/225* (2006.01)
*H01L 21/324* (2006.01)
(Continued)

(52) U.S. Cl.
CPC ..... *H01L 21/2253* (2013.01); *G01N 27/4146* (2013.01); *H01L 21/26513* (2013.01); *H01L 21/324* (2013.01); *H01L 51/002* (2013.01); *H01L 51/0595* (2013.01); *H01L 23/481* (2013.01); *H01L 51/0047* (2013.01); *H01L 51/0093* (2013.01)

(58) Field of Classification Search
CPC ........... H01L 21/2253; H01L 21/26513; H01L 21/324; G01N 27/4146
See application file for complete search history.

(56) References Cited

U.S. PATENT DOCUMENTS

| | | | |
|---|---|---|---|
| 2011/0018138 A1* | 1/2011 | Thet ...................... | B82Y 10/00 257/774 |
| 2012/0161333 A1 | 6/2012 | Thuaire et al. | |
| 2015/0243594 A1* | 8/2015 | Baillin .............. | H01L 21/76898 257/507 |

FOREIGN PATENT DOCUMENTS

WO  WO 2014/001290 A1  1/2014

OTHER PUBLICATIONS

French Preliminary Search Report dated Nov. 28, 2016 in French Application 16 53118 filed on Apr. 8, 2016 (with English Translation of Categories of Cited Documents).

(Continued)

*Primary Examiner* — Christine Enad
(74) *Attorney, Agent, or Firm* — Oblon, McClelland, Maier & Neustadt, L.L.P.

(57) ABSTRACT

Manufacturing of a device to connect at least one nano-object to an external electrical system, comprising a support provided with a semiconducting layer in which the first doped zones are formed at a spacing from each other, an external electrical system being connectable to the first doped zones, each first doped zone (8a, 8b) being in contact with a second doped zone on which a portion of the nano-object is located, the second doped zones being separated from each other and with a thickness less than the thickness of the first doped zones.

18 Claims, 7 Drawing Sheets

(51) Int. Cl.
    *H01L 21/265*     (2006.01)
    *G01N 27/414*     (2006.01)
    *H01L 51/00*     (2006.01)
    *H01L 51/05*     (2006.01)
    *H01L 23/48*     (2006.01)

(56) References Cited

OTHER PUBLICATIONS

Ma Han Thu Lwin, et al., "Silicon on insulator nanoscale backside interconnects for atomic and molecular scale circuits", Journal of Vacuum Science and Technology, vol. 28, (5), 2010, 7 pgs.
B. Weber, et al., "Ohm's Law Survives to the Atomic Scale", Science, vol. 335, 2012, 5 pgs.
Johnny C. Ho, et al., "Controlled nanoscale doping of semiconductors via molecular monolayers", Nature Materials, vol. 7, 2008, 16 pgs.
M.Y. Simmons, et al., "Scanning probe microscopy for silicon device fabrication", Molecular Simulation, vol. 31, (6-7), 2005, 11 pgs.

\* cited by examiner

DEVICE FOR CONNECTING AT LEAST ONE NANO-OBJECT AND METHOD OF MANUFACTURING IT

TECHNICAL DOMAIN AND PRIOR ART

This application relates to a device for connecting nano-objects to at least one external electrical system and a method of manufacturing such a device.

"Nano-objects" refers to objects for which at least one of the dimensions is within the interval from 0.1 nm to 1000 nm and more particularly from 1 nm to 100 nm and this category of nano-objects includes particularly nanoparticles (organic or inorganic), nano-wires, molecules or associations of molecules, and particularly biological molecules such as viruses and bacteria.

The objective nowadays is to characterise increasingly small nano-objects or to make structures at the scale of a nanometre. Therefore a device has to be fabricated to measure these nano-objects electrically and to be able to connect them to an external electrical system configured to make an electrical test of the nano-objects.

Document US 2012/0161333 A1 for example discloses an electrical connection of a nano-object using connecting elements passing through the back face of a substrate, the nano-object itself being placed on doped zones formed in a semiconducting surface layer located on the front face of the substrate and with a determined spacing between the nano-objects.

There is a problem in making these doped zones.

In particular, when dopants are implanted in the surface layer, the surface of this layer is damaged which has the consequence of degrading the electrical contact between the nano-object and the doped zones.

Furthermore, precise control over the spacing between doped zones in which the nano-object will be placed is particularly hard to obtain when the volume of the doped zone is large.

These problems become particularly important because we usually try to make doped zones sufficiently large so that a good quality electrical contact can be made.

The question that arises is to make a new device to connect a nano-object and a new method of making such a device improved with regard to the problems mentioned above.

PRESENTATION OF THE INVENTION

One embodiment of this invention is a method of making a device to connect at least one nano-object to an external electrical system, the method including:

a) forming first doped zones on which the external electrical system can be connected in a semiconducting layer of a support, the first doped zones having a thickness $e_1$, b) forming second doped zones between the first doped zones, each first doped zone being in contact with one of said second doped zones, the thickness $e_2$ of the second doped zones being less than said first thickness $e_1$, then c) placing a nano-object on the second doped zones.

The order of steps a) and b) can be reversed. Thus, doped zones called second doped zones can formed in which the nano-object will be placed, and doped zones called first doped zones are then formed to which the external electrical system can be connected.

Since these second doped zones are typically the result of one or several ion implantations at a smaller depth than the first doped zones, their surface damage after implantation will be less than that of the first doped zones. Reducing this damage and therefore the surface roughness of the semiconducting layer, improves the electrical contact of the nano-object on said support.

Typically, the dopant concentration in these second doped zones is limited to the near surface (of the order of a few nanometres) which facilitates control over the diffusion of dopants and consequently a precise definition of the distance G or the spacing G between the second doped zones.

The method may further include at least one thermal annealing after the formation of the second doped zones and before step c).

Such an annealing can activate the dopants in the first doped zones and the second doped zones and modify the surface condition of the doped zones. In particular, this reduces the roughness of the second doped zones that facilitates subsequent assembly of the nano-object on these zones.

A diffusion annealing of dopants can give precise control over the distance G. Such annealing can also be used to reconstruct a surface damaged by implantation.

Therefore thermal annealing is done under conditions (duration and temperature) such that a dopant activation function and a surface reconstruction function can be performed. The annealing can be done in two steps; a dopant activation step and another step for surface reconstruction.

The atmosphere under which the annealing is done can also be adapted so as to functionalise the second doped zones. For example, Si—H, Si—OH, Si—NH2, Si—CH3 and Si—COOH functions can be formed.

In particular, when the semiconducting layer is made of silicon, thermal annealing can be performed under a hydrogen atmosphere, so that Si—H bonds can be formed.

The support on which doped zones are formed may be a semiconductor on insulator type substrate comprising an insulating layer on which said semiconducting layer rests and a support layer on which the insulating layer rests.

According to one embodiment, the method may also comprise the following steps after step c):

assemble the semiconducting layer on another support, then, remove the support layer and the insulating layer from said support.

Thus, the semiconducting layer can be turned over and a device can be made in which the nano-object is encapsulated and thus protected.

Advantageously, the first doped zones can be formed partially using at least one implantation of the surface layer using an ion beam penetrating through a first face of the semiconducting layer, this first face being put into contact with said other support during said assembly and being opposite a second face in contact with the insulating layer, then after removal of the substrate support layer: at least one other implantation of the surface layer using an ion beam penetrating through the second face of the semiconducting surface layer, so as to extend the first doped zones. This enables implantation of deep semiconducting layers. Since the implantation depth is limited, the fact of implanting on the front face and then on the back face makes it possible to double the thickness of the implanted zone.

According to one possible embodiment, in which the support may be provided with an insulating layer on which the semiconducting layer is supported and a support layer on which the insulating layer is supported, the method may also comprise a step for the formation of conducting elements passing through the support layer and the insulating layer and coming into contact with the first doped zones.

Such conducting elements are made particularly when the thickness of the first doped zones is equal to the thickness of the semiconducting layer and therefore they are accessible from the back face of the support.

According to another aspect, this invention relates to a device to connect at least one nano-object to an external electrical system, the device comprising a support provided with a semiconducting layer in which the first doped zones are formed at a spacing from each other, an external electrical system being connectable to the first doped zones, each first doped zone being in contact with a second doped zone on which a portion of the nano-object is located, the second doped zones being separated from each other and being less thick than the first doped zones.

Thus, according to the invention, a device is provided with two types of doped zones: first doped zones adapted to hold elements such as electrodes, an external electrical system comprising read means, or test or control means, and second doped zones adapted to receive portions of at least one nano-object.

Providing second doped zones thinner than the first doped zones can give a better surface condition of the second doped zones and a more precise spacing.

The first doped zones can be provided with a surface seen from the top larger than that of the second doped zones.

Such an arrangement can give better electrical contact of nano-objects on the second doped zones while keeping the sizes of the first doped zones compatible with an external electrical system and a precise control of the spacing G between the second doped zones.

Thus, the dimensions of the first doped zones are adapted to the dimensions of elements of an external electrical system, for example elements with a micrometric size such as tips or electrodes, while the dimensions of the second doped zones are nanometric, adapted to nano-objects.

Advantageously, the thickness of the first doped zones may be equal to the thickness of said semiconducting layer, which in this case enables access by the lower face of said semiconducting layer.

The device may comprise several assemblies also called "groups" of first and second doped zones, in which each group can be connected a given size of nano-object that may be different from the size of nano-objects located on different groups of doped zones.

In this case, the first and second doped zones may be different sizes in different groups of doped zones. The spacing G or the distance G between second doped zones can vary in different groups of doped zones.

The first doped regions may be surrounded by an insulating region or an empty space, for example to avoid parasite signals from disturbing measurements made on the nano-object. This isolates the device from the remainder of the substrate. The insulating region is located outside the second doped zones with which the first doped zones are in contact.

The device may be equipped with several nano-objects.

According to one possible embodiment, the nano-object comprises a first portion located on one of said second doped zones and a second portion located on another of said second doped zones, said other doped zone comprising another portion of another nano-object.

Advantageously, the device may comprise a first portion located on one of said second doped zones with an N type doping and a second portion located on another of said doped second zones, said other second doped zone having a P type doping. This makes it possible to have a P/N junction of a component, for example of the diode, transistor or solar cell type.

BRIEF DESCRIPTION OF THE DRAWINGS

This invention will be better understood after reading the description of example embodiments given purely for information and that are in no way limitative, with reference to the appended drawings on which.

Identical, similar or equivalent parts of the different figures have the same numeric references to facilitate comparison between the different figures.

The different parts shown on the figures are not necessarily all at the same scale, to make the figures more easily understandable.

Furthermore, in the following description, terms that are dependent on the orientation such as "front", "back", "top", "bottom", etc. of a structure should be understood assuming that the structure is oriented as shown on the figures.

DETAILED PRESENTATION OF PARTICULAR EMBODIMENTS

Figure 1:
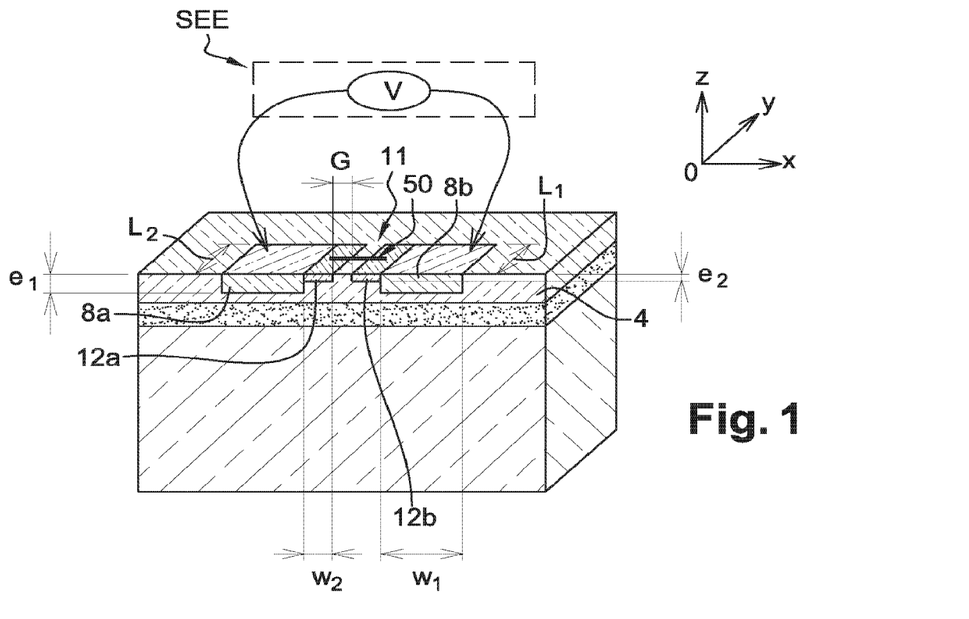
FIG. 1 illustrates a device according to one embodiment of this invention to connect at least one nano-object formed on a substrate with an external electrical system, the substrate comprising a semiconducting surface layer with first doped zones dedicated to reception of said nano-object and second doped zones with larger dimensions onto which the external electrical system will be connected.

Refer to FIG. 1 that contains a sectional view of a device to connect at least one nano-object to an external electrical system.

The nano-object 50 may be organic, for example DNA, or a biological molecule, a protein, a virus, or in the form of fibre(s), or inorganic, for example in the form of nanoparticles, or a semiconducting nano-wire, or an element made of a polymer material.

The electrical system SEE may be provided with a control device capable of emitting signals to the nano-object 50 and/or processing signals from the nano-object 50 or from a device to read electrical signals that will transit through the nano-object 50, or a test or characterisation device, for example capable of determining the electrical properties of the nano-object 50. Typically, the electrical system SEE is in the form of an integrated circuit.

The nano-object 50 is placed on a semiconducting surface layer 4 of a substrate 1, this surface layer for example being made of silicon or germanium or silicon germanium. In the example in FIG. 1, the semiconducting surface layer 4 is arranged on an insulating layer 3 itself placed on a semiconducting support layer 2.

In the semiconducting surface layer 4, first doped zones 8a, 8b at a spacing from each other are provided to hold elements of the external electrical system SEE, particularly electrodes, for example in the form of tips.

The first doped zones 8a, 8b are located each side of and in contact with second doped zones 12a, 12b on which ends or portions of the nano-object 50 are arranged. The second doped zones 12a, 12b are separated from each other by a space G of the order of several nanometres, and are located on each side of an undoped or slightly doped region 11 of the surface layer 4. "Slightly doped" means doping preferably less than $1^e14$ atoms/cm$^3$.

The thickness (also called height) $e_2$ of the second doped zones 12a, 12b located between the first doped zones 8a, 8b is less than the thickness or height $e_1$ of the first doped zones 8a, 8b. The thicknesses $e_1$, $e_2$ are measured parallel to the z axis of an orthogonal coordinate system [O; x; y; z] given on FIG. 1.

The areas $S_2=W_2 \times L_2$ of the second doped zones 12a, 12b as seen in a top view are also preferably smaller than the areas $S_1=W_1 \times L_1$ of the first doped zones 8a, 8b as seen in a top view. The areas $S_1$ and $S_2$ as seen in a top view are measured parallel to the principal plane of the substrate 1. In this context, a "principal plane" of the substrate 1 means a plane parallel to the [O; x; y] plane of the orthogonal coordinate system [O; x; y; z] given on FIG. 1. The lengths $L_1$, $L_2$ and the widths $W_1$, $W_2$ of the first doped zones 8a, 8b and the second doped zones 12a, 12b respectively are dimensions measured parallel to the [O; x; y] plane. The values of $L_1$ and $W_1$ are adapted as a function of the external electrical system used, while $L_2$ and $W_2$ are chosen as a function of the type of assembled nano-object.

Thus, the cross-section of the first doped zones 8a, 8b is typically greater than the cross-section of the second doped zones 12a, 12b. The cross-section is a section taken orthogonal to the [O; x; y] plane of the orthogonal coordinate system [O; x; y; z].

Due to fact that their dimensions are smaller than the dimensions of the first doped zones 8a, 8b, the roughness and/or less surface damage of the semiconducting layer 4 in the surface region of the second doped zones 12a, 12b is (are) lower than in the first doped zones 8a, 8b. The spacing G between the second doped zones 12a, 12b is also more precisely defined than the spacing between the first doped zones 8a, 8b.

A low roughness, particularly less than 1.5 A RMS measured by an AFM microscope with a studied area of 1×1 µm$^2$, allows the nano-object 50 to have good adhesion to the second doped zones 12a, 12b. Furthermore, the spacing G between the second doped zones 12a, 12b, is defined very precisely, in particular with a precision of the order of a few nanometres, typically 30 nm.

In one particular embodiment, the thickness $e_1$ of the first doped zones 8a, 8b corresponds to the thickness e of the semiconducting surface layer, so that in particular contact can be made on the first doped zones 8a, 8b at the bottom face of the semiconducting surface layer 4, in other words a face of this surface layer 4 against which there is a lower portion of the substrate 1, and in particular against which the insulating layer 3 extends.

Figure 2:
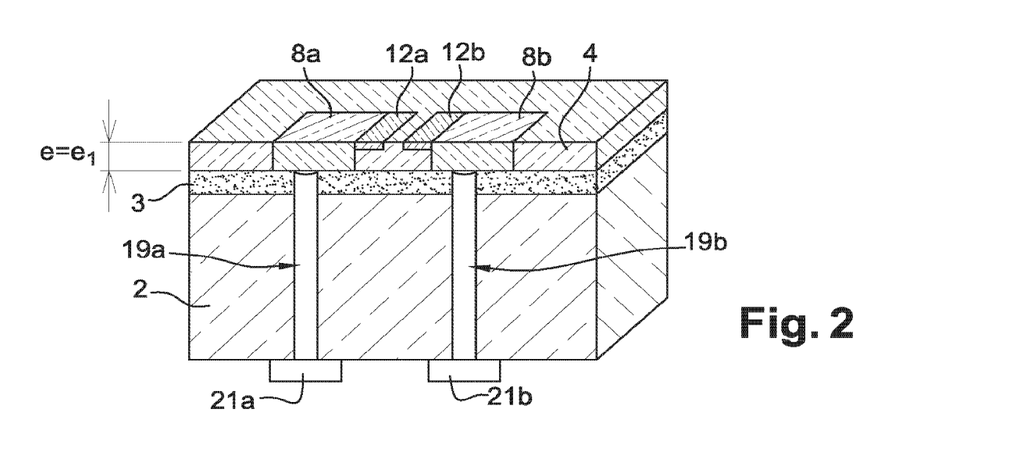
FIG. 2 illustrates a variant embodiment of the device according to the invention with through vias connected to doped zones and connecting these zones with a micronic sized electrical contact through the back face of the substrate.

Such a contact is illustrated on FIG. 2 showing a variant embodiment of the device in which the vertical conducting elements 19a, 19b commonly called "vias" pass through the support layer 2 and the insulating layer 3 to access the first doped zones 8a, 8b. These conducting elements 19a, 19b, open up on the back face of the substrate 1 and in this example are connected to conducting pads 21a, 21b formed on the back face of the substrate 1, in other words at a face of the substrate 1 opposite the front face, itself defined by the top face of the surface layer 4, in other words the face of the surface layer 4 opposite said bottom face. The length of the conducting pads 21a, 21b may correspond to the thickness of the support layer 2 and can typically be between one micron and several hundred microns or even several millimetres.

The vertical conducting elements 19a, 19b are typically made by the formation of holes passing through the support layer 2 of the substrate 1 until they expose first doped zones 8a, 8b, and these holes are then filled with a conducting material for example a metallic material such as Cu or W.

Figure 3:
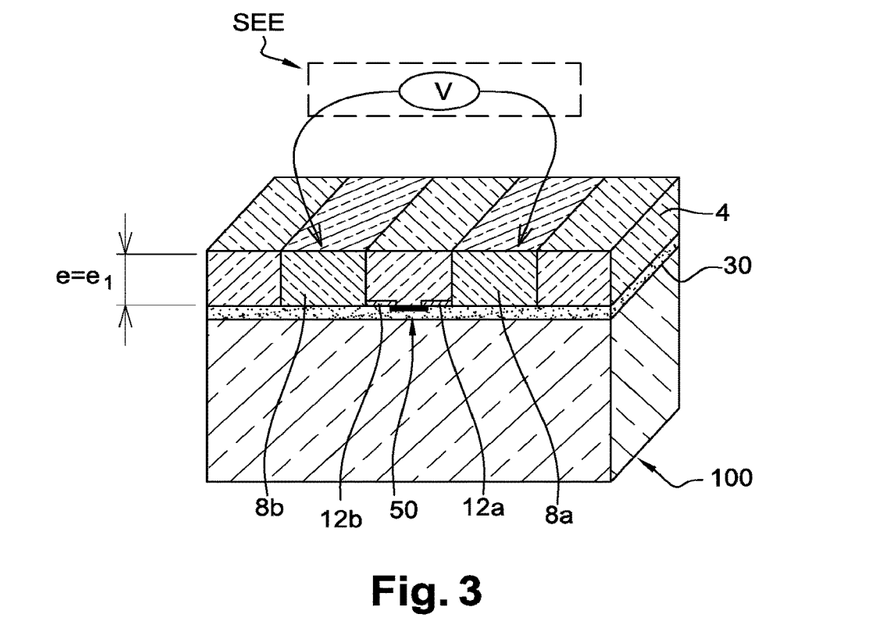
FIG. 3 illustrates a variant embodiment in which the nano-object is encapsulated.

According to another configuration illustrated on FIG. 3, the nano-object 50 and the second doped zones 12a, 12b are located at the bottom face of the semiconducting surface layer 4 and are thus inserted between a portion of the semiconducting surface layer 4 and a bottom portion of the substrate 1. The nano-object 50 is thus completely encapsulated and protected. The thickness $e_1$ of the first doped zones 8a, 8b is equal to the thickness e of the semiconducting surface layer 4 so that an external electrical system SEE can be connected to the first doped zones 8a, 8b on the front face of the substrate 1, without necessarily making use of additional conducting elements. This can make fabrication of the device easier and less expensive.

Such a configuration can be obtained by making a device like that illustrated on FIG. 1, then by assembling the substrate 1 to another support, for example to another substrate 100 that may be semiconducting or insulating, or semiconducting (for example silicon) covered by an insulating layer, for example an oxide layer. This other substrate 100 can possibly be flexible, for example it can be made of polyimide or graphene.

Figure 11:
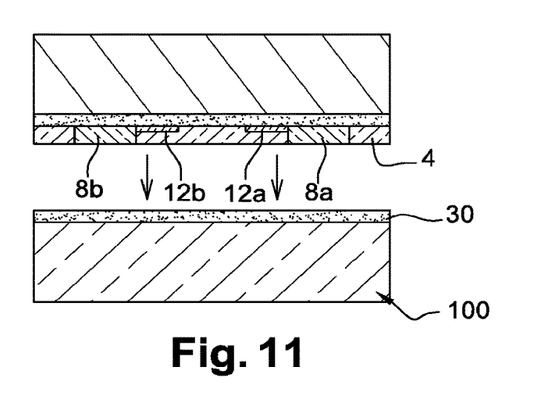
FIG. 11 illustrates a step in which the semiconducting surface layer is assembled with another support.

The assembly is then made for example by molecular bonding of the semiconducting surface layer 4 on an insulating layer 30 (FIG. 11) or by molecular bonding of an insulating coating formed on the semiconducting surface layer 4 with an insulating layer 30 of the other substrate 100. Once this assembly has been made, the lower portion of the original substrate 1 can be eliminated, in other words the insulating layer 3 and the support layer 2 can be removed. The assembly can also be made by gluing, for example a glue based on indium or using an adhesive polymer.

In this case, these first doped zones can be made in several steps, and particularly in several ion implantations. In particular, implantations made from the front face and from the back face make it possible to implant greater thicknesses than when the implantation is done from only one face.

Implanting from the front face before making a transfer, and then implanting from the back face after making a transfer, can double the thickness of the implanted zone. This also causes less surface damage on the front face of the substrate.

Thus, at least one first implantation of the semiconducting surface layer 4 is made from the front face of the substrate 1 before the assembly with another support is made. The next step is at least one second implantation of the second semiconducting surface layer 4 after making the assembly and removing the insulating layer 3. During the first implantation, first doped zones 8a, 8b can be implanted in only part of the semiconducting surface layer 4, for example of the order of several micrometres thick, the additional doping, for example also of the order of several micrometres thick, is then made to extend the first doped zones 8a, 8b over the entire thickness of the semiconducting surface layer 4, after this semiconducting surface layer 4 has been transferred to the other support.

It is possible to have several nano-objects on the same substrate 1.

Figure 4:
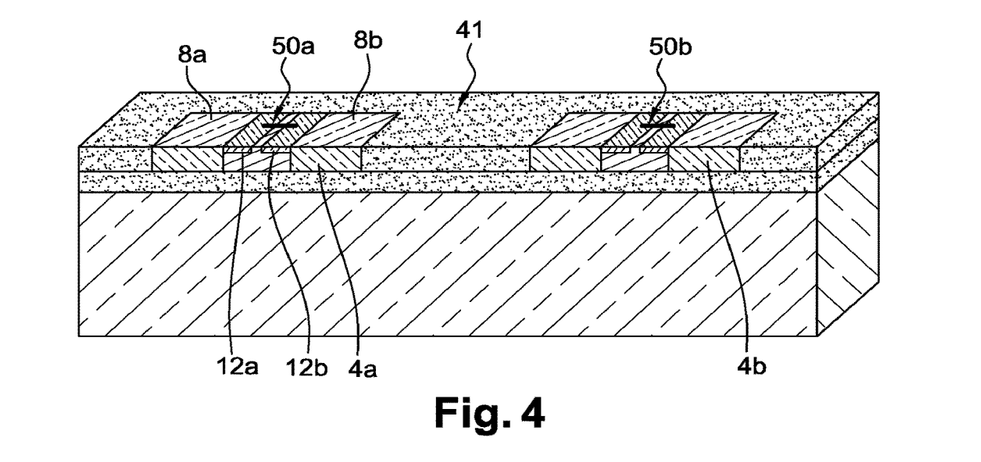
FIG. 4 illustrates a particular example embodiment in which the thickness of the first doped zones corresponds to the thickness of the semiconducting layer in which they are formed.

FIG. 4 illustrates an example embodiment in which the nano-objects 50a, 50b are located on semiconducting regions 4a, 4b respectively supported on a substrate and separated from each other by an insulating layer 41, for example made of SiO$_2$.

Such insulation can limit interference or disturbances between test or control or read signals for nano-objects 50a, 50b respectively. The insulating layer 41 can be distributed to completely surround the semiconducting regions 4a, 4b.

As a variant, in order to make such insulation, the insulating layer 41 can be replaced by an empty space, and in this case the semiconducting regions 4a, 4b are separated from each other by an empty space.

The second doped zones 12a, 12b can possibly be designed to hold several nano-objects each.

Figure 5:
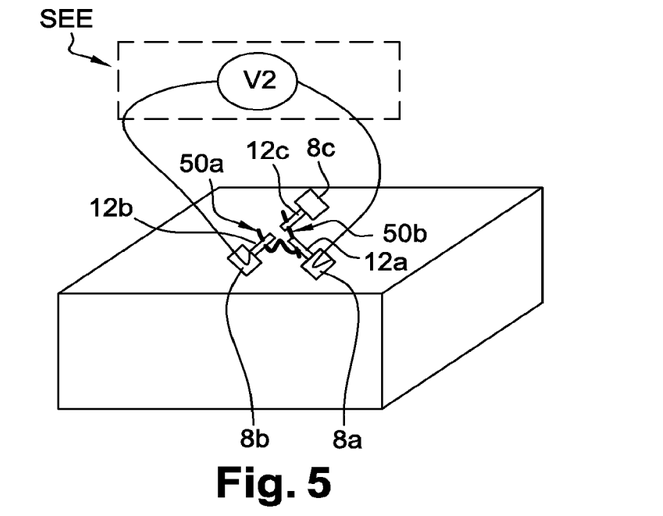
FIG. 5 illustrates an example embodiment in which the device comprises several nano-objects connected to the same doped zone.

In the example embodiment shown on FIG. 5, the device is also provided with two semiconducting regions, each comprising a first doped zone 8a, 8b, 8c for making contact with an external electrical system and a second semiconducting zone 12a, 12b, 12c to hold one or several nano-objects. In this case the device comprises a first nano-object 50a that has a portion connected to one doped zone 12b and to another doped zone 12a.

A second nano-object 50b comprises a portion connected to this other doped zone 12a and to a different doped zone 12c. The doped zone 12a is thus common to several nano-objects 50a, 50b. The electrical properties of the first nano-object 50a can be determined by making an electrical measurement between the doped zones 8a and 8b. If it is required to determine the electrical properties of the second nano-object 50b, the voltage measurement device can be placed on the doped zones 8a and 8c.

Figure 6:
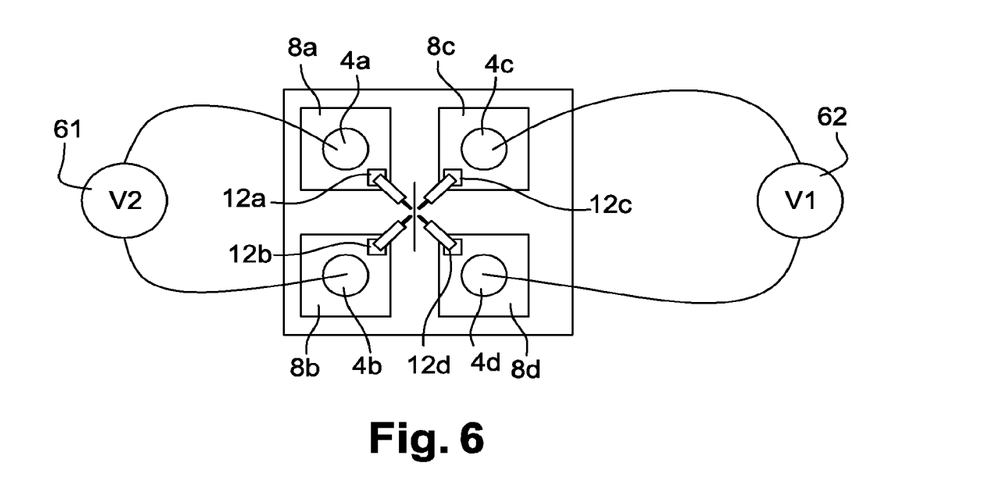
FIG. 6 illustrates an example embodiment with several doped zones and several nano-objects.

Another example configuration with several voltage measurement devices 61, 62 is shown on FIG. 6. The semiconducting surface layer in this case comprises four pairs of doped zones 8a-12a, 8b-12b, 8c-12c, 8d-12d in semiconducting regions 4a, 4b, 4c, 4d respectively, each pair comprising a doped zone 8a (8b, 8c, 8d respectively) to make contact with an external electrical system and a doped zone 12a, (12b, 12c, 12d respectively) to hold at least one nano-object.

A first voltage measurement device 61 is connected to the doped zones 8a, 8b of a first semiconducting region 4a and a second semiconducting region 4b, while a second voltage measurement device 62 is connected to the doped zones 8c, 8d of a third semiconducting region 4c and a fourth semiconducting region 4d.

Different dopings can be provided between the semiconducting regions.

For example, two pairs of doped zones 8a-12a, 8d-12d can be formed, doped with a first doping type, for example N type, and two other pairs of doped zones 8b-12b, 8c-12c can be formed, doped with a second doping type, for example P type. This type of device can be used to test a single nano-object with several doping types.

In one example in which the nano-objects are for example in the form of nano-wires deposited or fabricated between 2 electrodes with the same doping type (P or N), with these two pairs of doped zones, we can make a P-channel transistor and an N-channel transistor in the form of nano-wires, juxtaposed to each other. With these two pairs of doped zones, as a variant we can form two P/N junctions or P/N diodes, the nano object being placed between a P type electrode and an N type electrode. Therefore this facilitates management of components of the circuit, and the distance between devices can be reduced.

Figure 7:
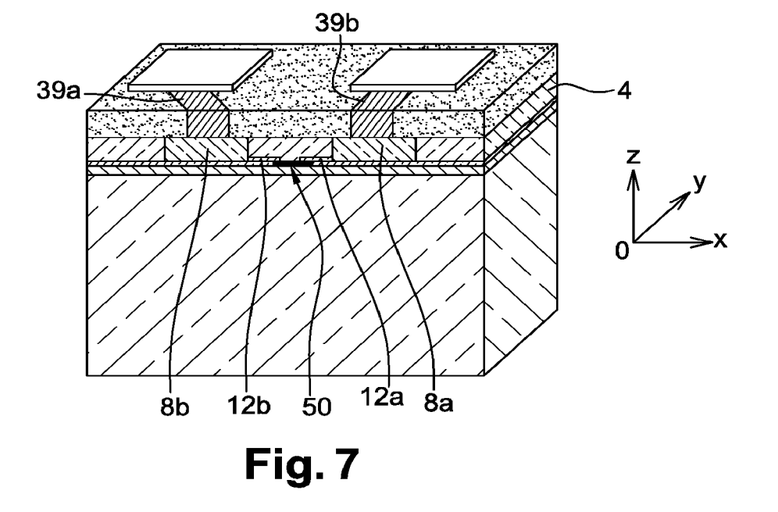
FIG. 7 illustrates an example embodiment in which the nano-object is covered with an insulating layer and in which a contact with the first doped zones is made using conducting tracks.

FIG. 7 illustrates a variant of the device in FIG. 3 in this case the top of the semiconducting surface layer 4 being protected by an insulating layer 3. This insulating layer 3 may be a layer derived from a semiconductor on insulator type substrate 1, on which there is initially the semiconducting layer 4 that is subsequently transferred to another substrate 100 before the support layer 2 of the semiconductor on insulator substrate is removed.

Conducting tracks 39a, 39b are formed to enable access to the first doped zones 8a, 8b on which an external electrical system will be connected and that are covered by the insulating layer 3.

Conducting tracks 39a, 39b can be formed extending between the side faces of the structure and come into contact with the first doped zones 8a, 8b. "Side faces" means faces that form a non-zero angle with the principal plane of the substrate, and particularly are orthogonal to it.

An example method of making a device like that described above for example with reference to FIG. 1, will now be described with reference to FIGS. 8A-8E.

The starting material for this method may be a semiconductor on insulator type substrate 1 (FIG. 8A) and particularly of the SOI (for « Silicon On Insulator ») or GeOI or SiGeOI, or sSOI ("strained Silicon On Insulator") type including a semiconducting support layer 2 coated with an insulating layer 3 called BOX ("Buried Oxide"), itself coated with a surface layer 4 made of a semiconducting material for example based on Si, or Ge or SiGe, the semiconducting material possibly being strained. The thickness of the surface layer 4 may for example be between 1 nm and several μm, while the thickness of SiO$_2$ layer is between 10 nm and several μm.

Figure 8A:
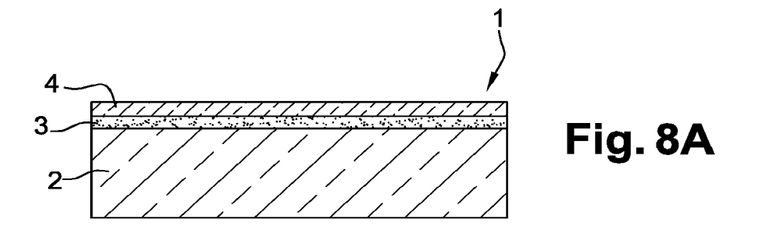
FIGS. 8A-8E illustrate cross-sectional views of an example method of making a device according to the invention.
Figure 8B:
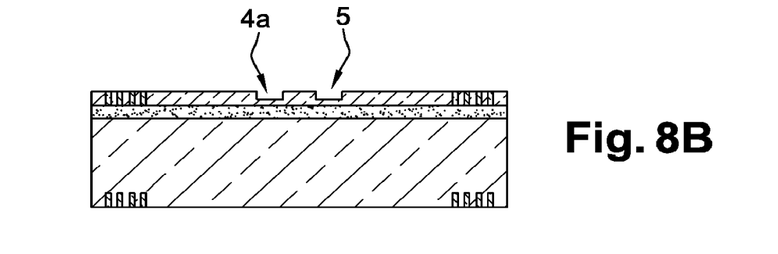

Patterns are then made in the surface layer 4, particularly in the form of trenches 5 to delimit one or several semiconducting regions of interest 4a in the surface layer 4, each semiconducting region of interest being capable of holding at least one nano-object (FIG. 8B).

The trenches 5 thus form localisation marks positioned around regions of interest 4a and can be used to localise these regions 4a. The region(s) of interest 4a may for example have an area equal to between 10 nm$^2$ and 1 mm$^2$, and particularly between 0.01 μm×0.01 μm and 10 μm×10 μm.

The trenches 5 can be made for example using a photolithography technique in which a resin mask is formed, and the semiconducting layer 4 is then etched through this mask and finally the resin mask is removed. Such trenches 5 can be detected by an imagery device for example provided with a microscope.

Figure 8C:
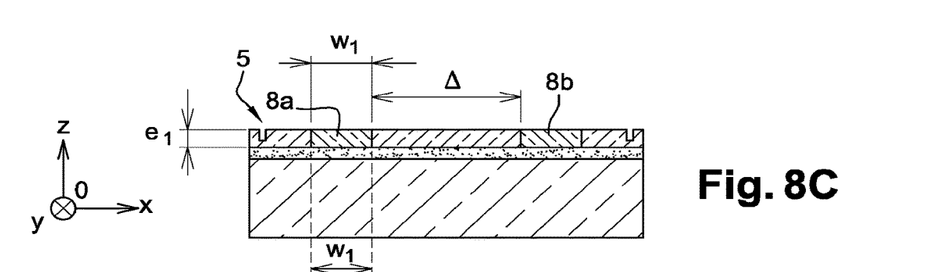

Distinct first doped zones 8a, 8b are then formed in the surface layer 4.

These doped zones are made in the region(s) of interest 4a, and in particular may be formed by ion implantation through a mask (not shown).

The first doped zones 8a, 8b made inside a perimeter delimited by trenches 5 or localisation marks can be brought into electrical contact with an external measurement device, and particularly the measurement tips of such a device. Typically, two P or N doped zones can be made in each semiconducting region of interest 4a. The distance Δbetween the two doped zones 8a, 8b can for example be between several nanometres and several hundred microns. The choice of the doping species of the first doped zones 8a, 8b is made as a function of the chosen application.

Implantation parameters (energy, dose, current) are chosen as a function of the thickness of the surface layer 4. The thickness $e_1$ of the first doped zones 8a, 8b can be equal to the thickness of the surface layer 4, in this case the entire thickness of the surface layer 4 is implanted.

For example, the following table lists examples of implantation conditions with different N or P type dopants, for a 205 nm thick semiconducting surface layer 4 made of silicon of an SOI substrate with a 400 nm BOX layer and a 725 μm support layer, for different dimensions of the first doped zones 8a, 8b.

| dopant | parameter | Min value | Max value | typically |
|---|---|---|---|---|
| Boron | Length $L_1$ | 1 μm | Several millimeters | 70-100 μm |
|  | Width $W_1$ | 1 μm | Several millimeters | 70-100 μm |
|  | Height or thickness $e_1$ | several nm | Several microns | 200 nm for $e_1$ = 200 nm |
|  | Energy | 3 keV | 500 keV | 30 keV/3E15/ atm/cm$^2$ |
|  | Dose | 1E12 atm/cm$^2$ | $1^E16$ at/cm$^2$ |  |
| Phosphorus | Length $L_1$ | 1 μm | Several millimeters | 70-100 μm |
|  | Width $W_1$ | 1 μm | Several millimeters | 70-100 μm |
|  | Height or thickness $e_1$ | several nm | Several microns | 200 nm |
|  | Energy | 3 keV | 500 keV | 85 keV/3E15 atm/cm$^2$ |
|  | Dose | 1E12 atm/cm$^2$ | $1^E16$ atm/cm$^2$ |  |
| Arsenic | Length $L_1$ | 1 μm | Several millimeters | 70-100 μm |
|  | Width $W_1$ | 1 μm | Several millimeters | 70-100 μm |
|  | Height or thickness $e_1$ | several nm | Several microns | 200 nm |
|  | Energy | 3 kev | 500 keV | 150 keV/3E15 + 50 keV 2E15 atm/cm$^2$) |
|  | Dose | 1E12 atm/cm$^2$ | 1E16 atm/cm$^2$ |  |

When the implantation(s) (are) finished, the roughness of the first doped zones 8a, 8b may be between 2 and 3 Å RMS ("Roughness mean square") measured by an Atomic Force Microscope (AFM) with a studied surface area of 1×1 μm$^2$ of silicon.

In the case particularly in which arsenic is implanted, at least two successive implantations are made in preference so that the implantation can be made uniformly throughout the entire thickness of the surface layer 4. The values given in the above table can be obtained by an ion implantation technique using an ion beam. Note that this dose corresponds to a concentration of dopants in the surface layer equal to between 1E15 atoms/cm$^3$ and 1E20 atoms/cm$^3$.

Figure 8D:
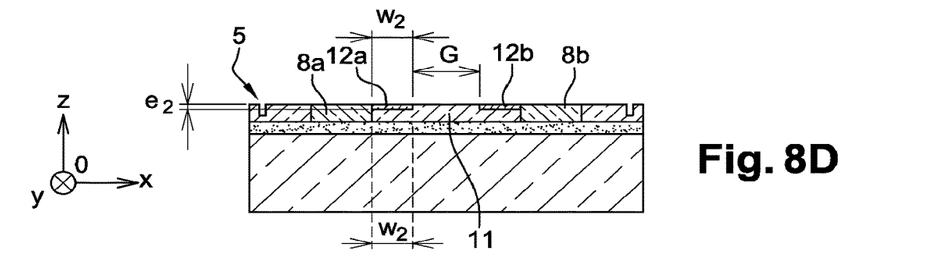

Distinct second doped zones 12a, 12b are then formed in the surface layer 4. These second doped zones 12a, 12b are made between the first doped zones 8a, 8b and are in contact with them. The dimensions of the second doped zones 12a, 12b and particularly the thickness $e_2$ are less than the dimensions and the thickness $e_1$ of the first doped zones 8a, 8b with which they are in contact.

The second doped zones 12a, 12b can extend over only part of the thickness of the surface layer 4 and their maximum concentration of dopants is located at a distance from the top face (i.e. the face opposite the face in contact with the BOX insulating layer 3) of the surface layer 4 that is less than the distance from the top face of the surface layer 4 at which the maximum concentration of dopants in the first zones 8a, 8b is located. The second doped zones 12a, 12b are intended to hold one or several nano-objects. The second doped zones 12a, 12b can be slightly doped and made by ion implantation or by another technique that can precisely control the distance G between the second doped zones 12a, 12b (FIG. 2D). The distance G between the second doped zones 12a, 12b may be between several Angstroms and several micrometres, typically between 10 nm and 1000 nm.

The surface of the surface layer 4 at the second doped zones 12a, 12b can be kept intact by doping these second zones 12a, 12b by diffusion, for example by depositing a molecule containing a doping species that is distributed in the semiconducting surface layer 4 during a later thermal annealing. Such doping by diffusion is presented for example in the document «Controlled nanoscale doping of semiconductors via molecular monolayers», by JOHNNY C. Ho, ROIE YERUSHALMI, ZACHERY A. JACOBSON ZHIYONG FAN,ROBERT L. ALLEY AND ALI JAVEY1, doi:10.1038/nmat2058.

This thus avoids a bombardment of the surface of the surface layer 4. As a variant, a shallow implantation or hot plasma immersion implantation technique can be used to limit damage to the surface of the surface layer 4 and to obtain a larger dose of dopants in the first nanometres at the surface.

For example, the following table lists implantation conditions with different N or P dopants for a 205 nm thick semiconducting surface layer 4 made of silicon of an SOI substrate with a 400 nm BOX layer and a 725 μm support layer, for different dimensions of the second doped zones 12a, 12b. The maximum concentration of dopants is located at a depth of 8 nanometres in the first semiconducting surface layer before the dopants are activated.

| dopant | parameter | Min value | Max value | typically |
|---|---|---|---|---|
| Boron | Length $L_2$ | several nm | 10 μm | 1 μm |
|  | Width $W_2$ | several nm | 10 μm | 300 nm |
|  | Thickness $e_2$ | several nm | Several hundred nm | 50 nm |
|  | Energy | 3 keV | 50 keV | 5 keV/ 1E15 at/cm$^2$ |
|  | Dose | $1^E12$ atm/cm$^2$ | 1E16 at/cm$^2$ |  |
| Phosphorus | Length $L_2$ | several nm | 10 μm | 1 μm |
|  | Width $W_2$ | several nm | 10 μm | 300 nm |
|  | Thickness $e_2$ | several nm | Several hundred nm | 50 nm |
|  | Energy | 3 keV | 50 keV | 6-8 keV/ 3E14 to 3E15 atm/cm$^2$) |
|  | Dose | $1^E12$ atm/cm$^2$ | 1E16 at/cm$^2$ |  |
| Arsenic | Length $L_2$ | several nm | 10 μm | 1 μm |
|  | Width $W_2$ | several nm | 10 μm | 300 nm |

-continued

| dopant | parameter | Min value | Max value | typically |
|--------|-----------|-----------|-----------|-----------|
|        | Thickness $e_2$ | several nm | Several hundred nm | 50 nm |
|        | Energy | 3 keV | 50 keV | As 15 keV |
|        | Dose | $1^E12$ atm/cm$^2$ | 1E16 at/cm$^2$ | 5E13 atm/cm$^2$ |

An undoped region 11 of the surface layer 4 or a region containing a remnant dopant is kept between the second zones 12a, 12b, such that the dopant concentration is preferably less than $1^E15$ atoms/cm$^3$.

Energy values used to make the second zones 12a, 12b, are typically less than the energy values used to make the first doped zones 8a, 8b.

When the implantation(s) is (are) complete, the roughness of the second doped zones 12a, 12b is typically less than the roughness of the first doped zones 8a, 8b and for example is between 1.5 and 2 A RMS measured by AFM microscope with a studied area of 1×1 µm$^2$ of silicon.

After formation of the first doped zones 8a, 8b and the second doped zones 12a, 12b, at least one thermal annealing is done, this thermal annealing possibly being composed of several steps.

Several successive thermal annealings can also be carried out, each annealing having its own function. The thermal annealing is adapted to perform at least one dopant activation function. In order to activate the dopants, the activation annealing is preferably done at high temperature for a short period, typically 1050° C. for several seconds. Such an annealing type can be done using an electron beam, laser beam, flash lamp or an RTP (Rapid Thermal Process) to limit diffusion of dopants in the surface layer 4 but also to enable evacuation of these dopants. It can be used to position the dopant as substitutional, thus allowing conduction of current.

Depending on the required application, thermal annealing or another heat treatment can also be provided so that the dose and distribution profile of dopants in the surface layer 4 can be modified by a diffusion phenomenon, typically between 950° C. and 1150° C. for several minutes. Such a heat treatment or thermal annealing can reduce the existing space G between the two doped zones 12a and 12b, so that the distance between them is on the scale of the nano-object to be studied and such that they can come into contact with these two doped zones 12a and 12b.

If the first doped zones 8a, 8b and/or the second doped zones 12a, 12b were made by implantation, the thermal annealing is also adapted so as to reconstruct the surface of the surface layer 4 and to reconstitute the crystallinity of the lattice.

In the case in which a zone of the order of several nanometres is required between the doped zones 11, the dopant activation and surface reconstruction annealing is done for example at a temperature between 500° C. and 1200° C., typically of the order of 950° C., with a duration of between a few seconds and a few hours, typically of the order of 8 minutes, in which the chosen annealing duration will be shorter for higher temperature.

At the end of the reconstruction thermal annealing(s), the roughness of the second doped zones 12a, 12b may for example be between 1 and 1.5 A RMS measured by AFM microscope with a studied area of 1×1 µm$^2$.

The dopant activation and crystalline structure reconstruction annealing may be done under an adapted atmosphere so that the semiconducting surface layer 4 can be functionalised. In this case, the activation and repair annealing may also have the function of facilitating subsequent bonding of the nano-object. "Functionalise" means create chemical bonds and preferably saturate bonds so that a nano-object can be deposited preferentially When the reconstruction and activation annealing is done under an atmosphere containing hydrogen ($H_2$) with an $H_2$ content for example between 1% and 100%, the surface of a silicon surface layer 4 can be saturated in Si—H bonds, which can subsequently facilitate making or bonding a nano-object, for example by UHV-STM (Ultra High Vacuum Scanning Tunneling Microscopy) type lithography. Such a surface with Si—H bonds is also particularly adapted to grafting of molecules or for example DNA strands.

A RP-CVD type reactor will preferably be used to implement such a functionalisation, by which a 100% hydrogen gas atmosphere can be obtained. In this case, the annealing is done at a temperature for example between 800° C. and 1200° C. for a duration of between 1 min and 30 min, preferably 950° C. during 7 minutes. The result obtained is thus a doped and reconstructed Si(001)-(2×1):H surface in which the distance G between the implanted zones can be of the order of several nanometres, in which the dopants will be activated and the surface perfectly smooth and saturated in Si—H bonds.

As a variant, instead of using an activation and surface repair annealing, a dopant activation annealing can be made followed by another reconstruction annealing adapted to repair the surface of the surface layer 4 and to distribute dopants in a 205 nm thick layer 4 of silicon. For this variant, a RTP activation annealing will be done for example, typically at 1050° C. for 1 s followed by a dopant diffusion annealing at 950° C. for 7 minutes and thus performing a smoothing function in an RP-CVD type reactor capable of obtained a 100% hydrogen gas atmosphere.

Figure 9A:
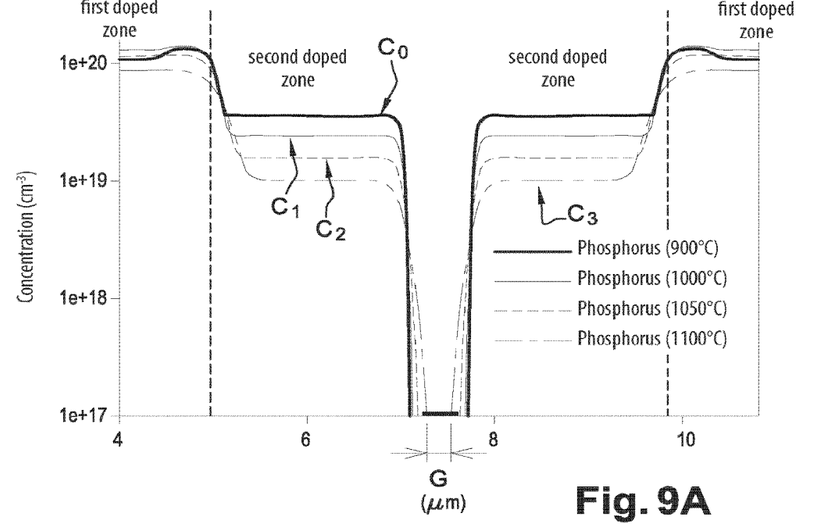
FIGS. 9A-9B represent examples of doping profiles for different temperatures.

FIG. 9A shows several examples of profiles $C_0, C_1, C_2, C_3$ for the dopant concentration in the surface layer after diffusion and activation of dopants, doping having been done with phosphorus after annealing at 950° C. (curve $C_0$) or 1000° C. (curve $C_1$) or 1050° C. (curve $C_2$) or 1100° C. (curve $C_3$) respectively for 7 minutes. First and second zones doped with a concentration of at least $10^{19}$ atoms/cm$^3$ can be obtained. The space G between the second doped zones in this example is between 0.2 µm and 0.6 µm. This distance can be further reduced to 30 nm for example, so as to connect smaller nano-objects.

Figure 9B:
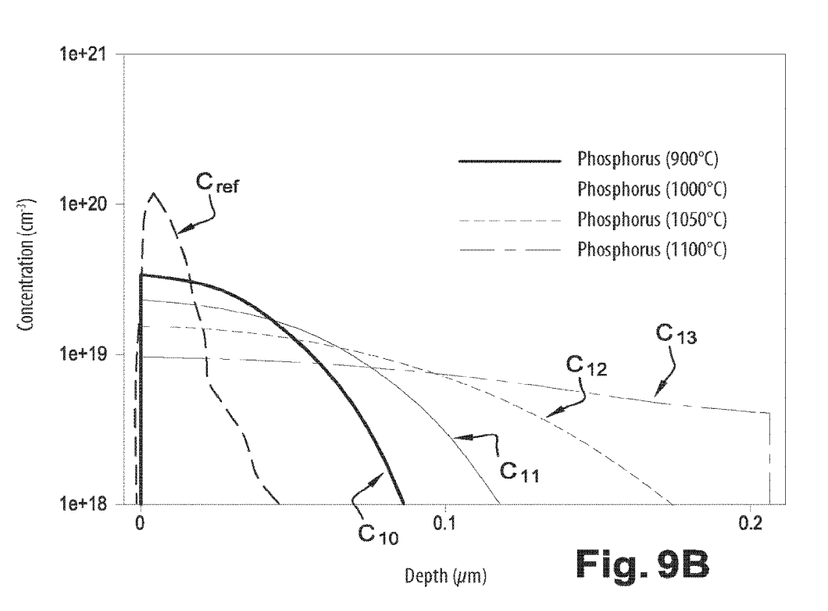

FIG. 9B illustrates several examples of dopant concentration profiles $C_{10}, C_{11}, C_{12}, C_{13}$ in the second doped zones 12a, 12b made by ion implantation with phosphorus at an energy of the order of 6 keV and a dose of 3E14 atoms/cm$^2$ for diffusion annealing temperatures equal to 950° C. (curve $C_{10}$) or 1000° C. (curve $C_{11}$) or 1050° C. (curve $C_{12}$) or 1100° C. (curve $C_{13}$) respectively for 7 minutes under hydrogen flux. One curve $C_{ref}$ is representative of a phosphorus concentration before annealing.

It is particularly useful to apply annealing at a temperature of 950° C. for a duration of 7 minutes so as to control the distance between the second doped zones 12a, 12b and to keep a sufficient concentration of phosphorus atoms so that the electrical signal of the nano-object can be conducted, because the diffusion length is then less than 0.03 µm while having a phosphorus concentration of more than $10^{19}$ at/cm$^3$. For example, in this example annealing at a temperature of less than 1100° C. is preferred.

Figure 8E:
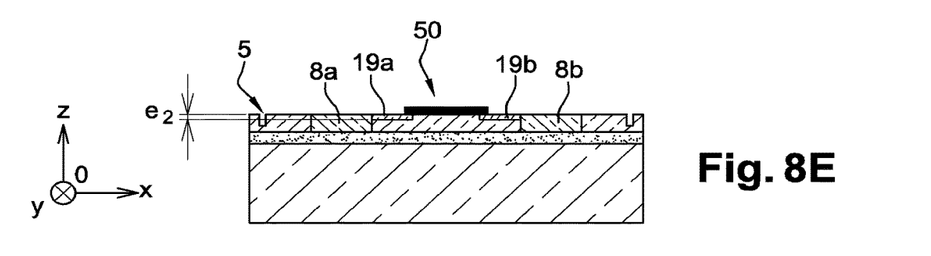

The result formed is then a nano-object 50 on the top face of the surface layer 4, in other words the surface on which the first doped zones 8*a*, 8*b* and 12*a*, 12*b* were made (FIG. 8E). The nano-object 50 is arranged so as to be in contact with the second doped zones 12*a*, 12*b* and possibly with a portion of the first doped zones 8*a*, 8*b*. The nano-object 50 may for example be in the form of organic or inorganic nano-particles, molecule(s), and particularly biological molecules such as a protein, DNA, a virus or an antibody. In an other example, the nano-object 50 may be a nano-wire.

"Formation" of the nano-object 50 includes particularly a surface modification (functionalisation) and/or grafting, or bonding, or a deposit possibly followed by structuring, for example by lithography.

Precise placement of the nano-object 50 on the second doped zones 12*a*, 12*b* can be automated through the use of equipment configured to detect positioning marks 5.

An encapsulation layer can then be formed so as to protect the nano-object 50. For an organic nano-object 50, the encapsulation layer may for example be based on resin. For an inorganic nano-object 50, a silicon or silicon oxide encapsulation for example could be formed.

Figure 10:
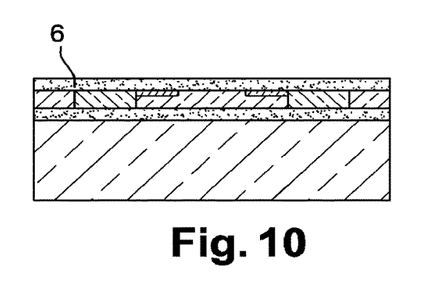
FIG. 10 illustrates an example embodiment in which the semiconducting surface layer is covered by an insulating protective layer.

Similarly, it would also be advantageous to provide a protection layer 6 on the semiconducting surface layer 4 prior to the steps to make the first doped zones 8*a*, 8*b* and the second doped zones 12*a*, 12*b*. This protection layer 6 may for example be made of silicon oxide and be done by thermal oxidation of the surface layer 4. The thickness of the protection layer 6 may for example be of the order of 10 nm.

Implantation steps of the surface layer 4 can then be carried out to form first and second doped zones 8*a*, 8*b*, 12*a*, 12*b*, during which the protection layer 6 can limit the surface damage of the surface layer (FIG. 10).

A device according to the invention as described above and provided with at least one nano-object placed on and in contact with thin doped zones can be used to make an OFET (Organic Field Effect Transistor) transistor structure with an organic nano-object and forming a transistor channel structure.

A nano-object device like that described above can also be used to make a switch or an amplifier, or a biological sensor (bio-sensor). In the case of a commutator, the nano-object(s) will act as a switch. In this case, the nano-object is typically in the form of a molecule placed on zones 12*a* and 12*b*. Part of the molecule is aligned on zones 12*a* and 12*b* under the effect of an electrical current, so that the current is conducted ("ON" position of the switch). When the current stops, part of the molecule is detached from zones 12*a* or *b*, and the current no longer passes ("OFF" position of the switch).

In the case of a biological sensor application, a nano-object is deposited between zones 12*a* and 12*b*, typically a molecule sensitive to an element, for example to a gas such as $CO_2$. When this element is in contact with the molecule, the element attaches to the molecule. This will then cause a modification to the electrical signal that can then be detected by the source SEE.

The invention claimed is:

1. A device to connect at least one nano-object to an external electrical system, said device comprising:
   at least a nano-object,
   a support provided with a semiconducting layer, said semiconducting layer comprising:
   first doped zones spaced from each other, the first doped zones forming connection zones for an external electrical system connectable to the first doped zones,
   second doped zones situated between said first doped zones, each second doped zone being in contact with a first doped zone, said second doped zones being separated from each other by a distance G and the second doped zones having a thickness less than the thickness of said first doped zones,
   wherein a first portion of said nano-object is located on one of said second doped zones and a second portion of said nano-object is located on another one of said second doped zones.

2. The device according to claim 1 wherein the first doped zones have a first surface and the second doped zones have a second surface smaller than the first surface.

3. The device according to claim 1 wherein the thickness of the first doped zones is equal to the thickness of said semiconducting layer.

4. The device according to claim 1, wherein the first doped zones are surrounded by an insulating region.

5. The device according to claim 1, wherein the support is a substrate comprising a stack composed of a support layer, an insulating layer and said semiconducting layer, the device being provided with conducting elements in contact with the first doped zones and passing through the support layer and the insulating layer.

6. The device according to claim 1, comprising another set of first doped zones and another set of second doped zones spaced from each other, each second doped zone of said another set being in contact with a first doped zone distinct from said another set, a second nano-object being connected with said second doped zones of said another set.

7. The device according to claim 1, wherein said nano-object comprises a first portion located on one of said second doped zones and a second portion located on another of said second doped zones, said other doped zone comprising another portion of another nano-object.

8. The device according to claim 1, wherein the nano-object comprises a first portion located on one of said second doped zones with N type doping and a second portion located on another of said second doped zones, said other doped zone having a P type doping.

9. A method of making a device to connect at least one nano-object to an external electrical system, the method including:
   forming first doped zones on which the external electrical system can be connected in a semiconducting layer of a support, the first doped zones having a thickness $e_1$, then
   forming second doped zones between the first doped zones such that each second doped zone is in contact with a first doped zone, the second doped zones being separated from each other by a distance G and having a second thickness less than said first thickness, then
   placing a nano-object on the second doped zones.

10. The method according to claim 9, wherein the first doped zones and the second doped zones are formed by ion implantation, the method including at least one thermal annealing after formation of the first and second doped zones and before placing said nano-object on the second doped zones, so as to activate dopants in the first and second doped zones and to define the distance G.

11. The method according to claim 10, wherein said at least one thermal annealing is done under an atmosphere that will functionalise the second doped zones.

12. The method according to claim 11, wherein the annealing(s) is (are) done under a hydrogen atmosphere.

13. The method according to claim 9, wherein the support is a substrate of the semiconductor on insulator type comprising an insulating layer on a support layer, on which said semiconducting layer is supported, the method further including the following steps after the step of placing said nano-object on the second doped zones:
assembling the semiconducting layer on another support, then,
remove the support layer and the insulating layer from said support.

14. The method according to claim 13, wherein the first doped zones are formed partially using at least one implantation using an ion beam penetrating through a first face of the semiconducting layer, said first face being put into contact with the support during said assembly and being opposite a second face in contact with the substrate, then after removal of the substrate:
at least one other implantation using an ion beam penetrating through the second face of the semiconducting layer, so as to extend the first doped zones.

15. The method according to claim 9, wherein the support comprises a support layer on which an insulating layer rests, the semiconducting layer being located on the insulating layer, the method further including a step in which conducting elements are formed in contact with the first doped zones and passing through the support layer and the insulating layer.

16. The method according to claim 9, wherein the thickness of the first doped zones is equal to the thickness of the semiconducting layer.

17. The method according to claim 9, wherein the first doped zones are formed by at least an implantation, the second doped zones being formed by shallow implantation or by a hot plasma immersion implantation.

18. The method according to claim 9, wherein the first doped zones are formed by at least an implantation, the second doped zones being formed by diffusion.

* * * * *